United States Patent [19]

Ovchinnikov et al.

[11] 4,058,618

[45] Nov. 15, 1977

[54] CERTAIN HYDANTOIN CONTAINING BACTERICIDES WHICH ARE RESISTANT TO SELF-HEATING

[76] Inventors: Viktor Georgievich Ovchinnikov, ulitsa Bazhova, 10, kv. 61; Nadezhda Petrovna Noritsa, ulitsa Avtozavodskaya, 21a, kv. 26; Maria Mefodievna Grib, ulitsa Bazhova, 10, kv. 30, all of Kiev; Nikolai Alexandrovich Kamennov, ulitsa Kievskaya, 20, kv. 28; Elena Konstantinovna Skvortsova, ulitsa Molodtsova, 8, korpus 2, kv. 131, both of Moscow, all of U.S.S.R.

[21] Appl. No.: 630,260

[22] Filed: Nov. 10, 1975

[51] Int. Cl.$^2$ .............................................. A01N 9/22
[52] U.S. Cl. .............................. 424/273 R; 252/106
[58] Field of Search ........................ 424/273; 252/106

[56] References Cited

U.S. PATENT DOCUMENTS

| | | | |
|---|---|---|---|
| 3,257,324 | 6/1966 | Wearn et al. | 252/99 |
| 3,346,446 | 10/1967 | Zsoldos | 424/150 |

OTHER PUBLICATIONS

Chemical Abstracts 65: 8680d (1966).

*Primary Examiner*—Leonard Schenkman
*Attorney, Agent, or Firm*—Steinberg & Blake

[57] ABSTRACT

A bactericide of the following composition, wt.%:
 1,3-dichloro-5,5-dimethylhydantoin, 19–25
 5,5-dimethylhydantoin, 10–19
 neutral sodium phosphates, 7–15
 sodium chloride and/or anhydrous sodium sulphate, 59–40
 alkylarylsulphonate and/or alkylsulphonate, 5–1.

The proposed bactericide exhibits resistance to self-heating, is safe in manufacture and storage, and is highly soluble in water, allowing for an active chlorine concentration in water of 4,000 to 5,000 parts per million. The bactericide has a powerful effect on microorganisms: 5 to 15 minutes of exposure to the bactericide at a concentration of 0.005 percent by weight kills *E. coli* and *Staphylococcus aureus*. Its toxicity is low: LD$_{50}$ = 2,000 to 3,000 mg/kg of weight for warm-blooded animals.

The bactericide of the invention may find application for washing and disinfecting various surfaces.

9 Claims, No Drawings

CERTAIN HYDANTOIN CONTAINING BACTERICIDES WHICH ARE RESISTANT TO SELF-HEATING

The present invention relates to a bactericide on the basis of 1,3-dichloro-5,5-dimethylhydantoin.

The proposed bactericide may find application for washing and disinfecting various surfaces.

It is common knowledge to those skilled in the art that 1,3-dichloro-5,5-dimethylhydantoin (to be referred to hereinafter at DCDMH) containing about 72 percent active chlorine is a potent oxidizing and chlorinating agent widely employed as an effective bactericide, fungicide, sporicide and bleach distinguished by virtue of its high moisture resistance. DCDMH is slightly soluble in water (about 0.1 percent at 20° C.). The low solubility of DCDMH makes it difficult to prepare process solutions and in some cases prevents attaining a desired concentration of DCDMH in process solutions, necessitating the use of higher temperatures at which the compound becomes more water-soluble and the rate of its dissolution rises (0.6 percent at 60° C.). At higher temperatures, however, the vapour of the solution irritates the respiratory tract and the mucosa; furthermore, it is not always possible to prepare and use hot solutions, particularly for the purpose of general disinfection.

The poor water wettability of DCDMH likewise reduces its rate of dissolution and promotes film formation on the surface of the solution. Still further disadvantages of DCDMH consist in its lack of detergency and its relatively high toxicity ($LD_{50} = 500$ mg/kg of weight).

It is known in the art to employ an oxidizing and bactericidal agent on the basis of DCDMH designed for bleaching and washing fabrics. This agent containing 8 percent active chlorine has the following formulation, wt.%:

DCDMH, 12
sodium tripolyphosphate, 25
alkylsulphonate 5
anhydrous sodium sulphate, 58.

The foregoing agent exhibits detergency and gives a basic reaction. Its high pH value constitutes no obstacle to washing or bleaching, so the agent is quite effective for the mentioned purposes at a concentration of 1.25 g/lit (0.1 percent active chlorine by weight).

However, such an agent is unsuitable for disinfection purposes, for the highest attainable concentration of active chlorine in the solution at room temperature does not exceed 0.08 to 0.10 percent by weight, a markedly inadequate level what with the basic reaction of the process solution. Furthermore, the bactericide contains too little of the active principle, viz. DCDMH.

It is further known in the art to employ a bactericide used primarily for disinfection purposes, which contains about 12 percent active chlorine. It has the following composition, wt.%:

DCDMH, 17
5,5-dimethylhydantoin, 8
sodium laurylsulphate, 5
$NaH_2PO_4$, 70.

This latter compound provides for a sufficiently high concentration of active chlorine in the process solution and can thus be put to effective use as a disinfectant. On the other hand, it is lacking in detergency the reason for which should be sought in its high content of acid sodium phosphate making for the bactericidal effect but adversely affecting detergency.

There also exists a detergent with bactericidal properties which is intended above all for washing highly contaminated surfaces. This latter compound, which contains about 11 percent active chlorine, has the following composition, wt.%:

DCDMH, 15
alkylsulphonate, 25
sodium tripolyphosphate, 50
anhydrous sodium sulphate, 10.

This agent provides for a very high alkalinity of the process solution and displays excellent detergency, but presents a poor bactericide, for its maximum concentration of active chlorine in the process solution is only 0.08 to 0.10 percent by weight patently inadequate for disinfection in an alkaline medium.

In order to impart detergency and wettability to DCDMH, the latter is used in combination with surface-active agents.

The solubility of DCDMH is improved by adding 5,5-dimethylhydantoin to the composition.

To improve the detergency of the composition, large quantities of alkali phosphates are added thereto; whereas addition of large quantities of acid phosphates improves the bactericidal properties of the compound. Thus, one property is enhanced at the expense of the other depending on the purpose of the composition. However, whatever the ultimate purpose of any composition of this kind, it invariably contains a high proportion of phosphates. Hence, if these compounds are widely used, said phosphates contained therein massively contaminate water reservoirs, causing vigorous propagation of blue-green algae.

Another disadvantage of all these compositions consists in their relatively low level of DCDMH and, hence, active chlorine combined with a high content of inert materials.

A mixture of DCDMH with surfactants, an insoluble inorganic salt or an anhydrous salt or a mixture thereof capable of forming crystal hydrates and acid phosphates, is one of the bactericides used primarily for disinfection purposes. Said mixture is obtained by comminuting all the components together to a particle size of less than 10 microns, preferably less than 6 microns. This composition is distinguished by a high rate of dissolution (from several seconds to 1 minute) and contains a large quantity of active chlorine.

This latter bactericide is not devoid of disadvantages either; its DCDMH, or active chlorine, component is poorly soluble in water; besides, the acid phosphate present in the composition and the relatively low content of the surfactant therein largely detract from its detergency. For these reasons, the composition is ineffective as far as highly contaminated items or resistant microorganisms are concerned. Furthermore, the high level of active chlorine in said latter composition renders it unstable in storage; and the manufacturing technique involving comminution to a particle size of less than 10 microns adversely affects the economics of the process.

It is an object of the present invention to provide an agent with a high content of active chlorine exhibiting resistance to self-heating, adequate solubility, high bactericidal activity, high rate of dissolution and satisfactory detergency, and forming no film on the surface of the solution upon dissolution in water.

The foregoing object is attained in a bactericidal agent which, in accordance with the invention, has the following composition, wt.%:
1,3-dichloro-5,5-dimethylhydantoin, 19-25
5,5-dimethylhydantoin, 10-19
neutral sodium phosphates, 7-15
sodium chloride and/or anhydrous sodium sulphate, 59-40
alkylarylsulphonate and/or alkylsulphonate, 5-1.

It is preferred that the bactericidal agent of this invention have the following composition, wt.%:
1,3-dichloro-5,5-dimethylhydantoin, 22.1
5,5-dimethyhydantoin, 14.4
neutral sodium phosphates, 10.0
sodium chloride, 50.0
alkylarylsulphonate, 3.5.

It is possible to employ a bactericidal agent having the following composition, wt.%:
1,3-dichloro-5,5-dimethylhydantoin, 22.1
5,5-dimethylhydantoin, 14.4
neutral sodium phosphates, 10.0
sodium chloride, 50.0
alkylsulphonate, 3.5.

It is desirable to employ a bactericidal agent having the following composition, wt.%:
1,3-dichloro-5,5-dimethylhydantoin, 19.1
5,5-dimethylhydantoin, 12.4
neutral sodium phosphates, 15.0
anhydrous sodium sulphate, 50.0
alkylarylsulphonate, 3.5.

The proposed bactericidal agent preferably has the followings composition, wt.%:
1,3-dichloro-5,5-dimethylhydantoin, 19.1
5,5-dimethylhydantoin, 12.4
neutral sodium phosphates, 15.0
anhydrous sodium sulphate, 50.0
alkylsulphonate, 3.5.

It is further possible to employ a bactericidal agent having the following composition, wt.%:
1,3-dichloro-5,5-dimethylhydantoin, 22.1
5,5-dimethylhydantoin, 14.4
neutral sodium phosphates, 10.0
sodium chloride and anhydrous sodium sulphate, 50.0
alkylsulphonate, 3.5.

It is likewise possible to make use of a bactericidal agent of the following composition, wt.%:
1,3-dichloro-5,5-dimethylhydantoin, 22.1
5,5-dimethylhydantoin, 14.4
neutral sodium phosphates, 10.0
sodium chloride and anhydrous sodium sulphate, 50.0
alkylarylsulphonate, 3.5.

It is recommended to employ a bactericidal agent having the following composition, wt.%:
1,3-dichloro-5,5-dimethylhydantoin, 22.1
5,5-dimethylhydantoin, 14.4
neutral sodium phosphates, 10.0
sodium chloride, 50.0
alkylarylsulphonate and alkylsulphonate, 3.5.

It is also useful to employ a bactericidal agent having the following composition, wt.%:
1,3-dichloro-5,5-dimethylhydantoin, 19.1
5,5-dimethylhydantoin, 12.4
neutral sodium phosphates, 15.0
anhydrous sodium sulphate, 50.0
alkylarylsulphonate and alkylsulphonate, 3.5.

Our research revealed that DCDMH and its combinations with other substances, particularly potential reducing agents which include the surfactants, are liable, under certain conditions, to undergo spontaneous decomposition and self-heating.

Our investigations clearly show that of the surfactants only alkylarylsulphonates and alkylsulphonates satisfactorily combine with DCDMH to form relatively stable compositions, although here, too, there is a risk of decomposition which, given certain conditions, causes accelerating spontaneous heating of the mixture. The behaviour of DCDMH-base mixtures upon heating was studied by the following method. A 3-g sample was placed in a test tube, the test tube was immersed in an oil bath so that the sample in the test tube is level with the oil in the bath, and then the oil bath was heated at a gradient of 1° to 3° C. per minute, simultaneously measuring the temperatures of the sample in the test tube and of the oil in the bath using two thermometers. As the temperature of the bath gradually increased, the readings of the two thermometers started to diverge, the oil temperature being several degrees higher than that of the sample.

Where the sample failed to undergo self-heating, the above-mentioned divergence in the readings of the two thermometers held until the heating was discontinued. But if the sample proved unstable and underwent spontaneous self-heating, at a certain temperature, referred to hereinafter as critical, the two readings were first equalized, then the sample temperature rose to a level several degrees higher than that of the bath, after which the sample temperature started to rise rapidly (within fractions of a minute), sometimes as high as 300° C., the temperature rise being accompanied by resinification, liberation of gas and spattering of the sample.

The experimental data for DCDMH mixtures with alkylarylsulphonate tested under the aforementioned conditions are given in Table 1.

Table 1

| Test No. | Composition of the sample, wt.% | | Additional experimental condition | Self-heating temperature, °C | | Temperature jump, °C |
| --- | --- | --- | --- | --- | --- | --- |
| | DCDMH | alkylarylsulpho-nate | | beginning | end | |
| 1. | 100 | 0 | Precomminuted components were mixed | 195 | 300 | 105 |
| 2. | 0 | 100 | " | — | — | — |
| 3. | 91 | 9 | " | 190 | 240 | 50 |
| 4. | 80 | 20 | " | 130 | 205 | 75 |
| 5. | 60 | 40 | " | 113 | 180 | 67 |
| 6. | 30 | 70 | " | 90 | 176 | 86 |
| 7. | 30 | 70 | The sample was immersed in a bath heated to 80° C. | 50 | 142 | 92 |
| 8. | 91 | 9 | The sample was priorly packed | 190 | 270 | 80 |
| 9. | 91 | 9 | 10 wt.% water was added*/ | 160 | 276 | 116 |
| 10. | 91 | 9 | The sample was prepared by evaporating an aqueous suspension under vacuum | 134 | 190 | 56 |

Table 1-continued

| Test No. | Composition of the sample, wt.% | | Additional experimental condition | Self-heating temperature, °C | | Temperature jump, °C |
|---|---|---|---|---|---|---|
| | DCDMH | alkylarylsulpho-nate | | beginning | end | |
| 11. | 91 | 9 | The components were laid in unmixing layers | 127 | 270 | 143 |

*/Upon wetting, the 3-g sample was heated by 5° C.

As follows from the table, under certain conditions the critical temperature is only 50° C., i.e. it is easily attainable while preparing mixtures due to mechanical warming up. When moisture gets into the mixture, the latter is heated.

Accidental heating or self-heating of the agent induces a high temperature at one point of the preparation which involves the whole bulk of the product in vigorous decomposition.

To improve DCDMH solubility in water, it is admixed with 5,5-dimethylhydantoin (to be referred to hereinafter as DMH). Such an equimolar mixture DCDMH + DMH undergoes self-heating upon being heated to 186° C., giving a temperature jump of up to 310° C.

Here is an illustration of the way various additives affect the critical temperature and the size of the temperature jump for an equimolar mixture of DCDMH with 5,5-dimethylhydantoin (DCDMH + DMH). Addition to this mixture of mineral dopants with a view to diluting the mixture, including soluble mineral salts forming no crystal hydrates as well as anhydrous mineral salts forming crystal hydrates and staying inert with respect to DCDMH, fails to prevent such mixtures from self-heating, as illustrated in Table 2.

Table 2

| DCDMH + DMH level, wt.% | Level of inorganic salt, wt.% | Self-heating temperature, °C | | Temperature jump °C |
|---|---|---|---|---|
| | | beginning | end | |
| | | sodium chloride | | |
| 70 | 30 | 180 | 278 | 98 |
| 60 | 40 | 190 | 274 | 84 |
| 50 | 50 | 195 | 270 | 75 |
| 40 | 60 | 197 | 263 | 68 |
| 30 | 70 | 201 | 251 | 50 |
| 20 | 80 | 205 | 230 | 25 |
| | | anhydrous sodium sulphate | | |
| 70 | 30 | 167 | 270 | 103 |
| 60 | 40 | 176 | 270 | 94 |
| 50 | 50 | 174 | 252 | 76 |
| 40 | 60 | 170 | 240 | 70 |
| 30 | 70 | 179 | 230 | 51 |
| 20 | 80 | 200 | 228 | 28 |

The reduction in the magnitude of the temperature jump as the salt concentration rises can be ascribed to the drop in the absolute quantity of DCDMH in the experiments (as pointed out above, the aliquot was invariably equal to 3 g). Addition to the mixture of DCDMH+DMH and sodium salts to the extent of up to 80 percent by weight likewise fails to improve its temperature stability, whereas neutral sodium phosphates succeed in suppressing the self-heating phenomenon, as illustrated by Table 3.

Table 3

| Level of DCDMH + DMH, wt. % | Level of neutral sodium phosphates, wt. % | Self-heating temperature, °C | | Temperature jump, °C |
|---|---|---|---|---|
| | | beginning | end | |
| | | sodium triphosphate | | |
| 70 | 30 | 160 | 240 | 80 |
| 60 | 40 | 161 | 225 | 64 |
| 5 50 | 50 | — | — | — |
| | | sodium tripolyphosphate | | |
| 70 | 30 | 195 | 242 | 47 |
| 60 | 40 | 190 | 222 | 32 |
| 50 | 50 | 193 | 222 | 29 |
| 40 | 60 | 224 | 238 | 14 |
| 30 | 70 | — | — | — |

Substitution of sulphonate for some (several percentage points) neutral phosphates fails to affect the mixture stability, as illustrated by Table 4.

Table 4

| Composition of the mixture, wt.% | | | Self-heating temperature, °C | | Temperature jump, °C |
|---|---|---|---|---|---|
| DCDMH +DMH | neutral sodium phosphate | alkylaryl-sulphonate | beginning | end | |
| 80 | 16.5 | 3.5 | 191 | 269 | 79 |
| 70 | 26.5 | 3.5 | 189 | 253 | 64 |
| 60 | 36.5 | 3.5 | 190 | 253 | 63 |
| 50 | 46.5 | 3.5 | 190 | 260 | 70 |
| 40 | 56.5 | 3.5 | 207 | 248 | 41 |
| 30 | 66.5 | 3.5 | — | — | — |

However, large amounts of neutral sodium phosphates cannot be employed in disinfecting preparations, as they alkalize the latter and adversely affect their bactericidal properties.

Besides, the phosphates used in bactericides often find their way in massive quantities to natural water reservoirs, causing vigorous propagation of blue-green algae.

Experiments helped find ways of reducing the overall level of mineral components in the proposed compositions, as illustrated by Table 5.

Table 5

| Composition of the mixture, wt.% | | | | | Self-heating temperature, °C | |
|---|---|---|---|---|---|---|
| DCMDH+DMH | alkylaryl-sulphonate | sodium tripoly-phosphonate | sodium chloride | anhydrous sodium sulphate | beginning | end |
| 50 | — | 15 | 35 | — | 165 | 288 |
| 50 | — | 20 | 30 | — | 207 | 282 |
| 50 | — | 30 | 20 | — | 197 | 265 |
| 46.5 | 3.5 | 20 | 30 | — | 195 | 226 |
| 46.5 | 3.5 | 30 | 20 | — | 195 | 235 |
| 36.5* | 3.5 | 30 | 30 | — | — | — |
| 36.5 | 3.5 | 20 | 40 | — | — | — |
| 36.5 | 3.5 | 10 | 50 | — | — | — |

Table 5-continued

| DCMDH+DMH | Composition of the mixture, wt.% | | | | Self-heating temperature, °C | |
| --- | --- | --- | --- | --- | --- | --- |
| | alkylaryl-sulphonate | sodium tripoly-phosphonate | sodium chloride | anhydrous sodium sulphate | beginning | end |
| 36.5 | 3.5 | 5 | 55 | — | 195 | 250 |
| 46.5 | 3.5 | 30 | — | 20 | 205 | 260 |
| 36.5 | 3.5 | 30 | — | 30 | 190 | 246 |
| 36.5 | 3.5 | 20 | — | 40 | 195 | 253 |
| 31.5** | 3.5 | 15 | — | 50 | — | — |
| 36.5 | 3.5 | 10 | 30 | 20 | — | — |

*22.1% DCDMH and 14.4% DMH
**19.1% DCDMH 12.4% DMH

As follows from Table 5, the maximum allowable quantity of DCDMH at which the mixture is resistant to self-heating is 19 percent by weight for neutral sodium phosphates combined with anhydrous sodium sulphate, and between 22 and 25 percent by weight for neutral sodium phosphates combined with sodium chloride. More detailed experiments gave a refined value of 25 percent by weight. At a lower level of DCDMH, the composition loses some of its effectiveness against microorganisms. The equimolar quantity of 5,5-dimethylhydantoin compatible with the above range of DCDMH concentrations lies between 14.3 and 16.2 percent by weight. It was shown experimentally, however, that the level of 5,5-dimethylhydantoin could be safely reduced to 10 percent by weight without affecting DCDMH solubility. Yet the level of DMH should be desirably increased, it being an effective scarifier in the course of dissolution. However, should the level of DMH exceed 19 percent by weight, the composition loses its resistance to self-heating the reason for which should be sought in the increased proportion of a readily oxidizable organic component.

The data of Table 4 suggest that at a level of neutral sodium phosphates from 5 to 10 percent by weight, the mixture loses its resistance to self-heating. It was experimentally demonstrated that 7 percent by weight was the minimum permissible level of neutral sodium phosphates in the composition. It further follows from Table 4 that, as far as the resistance of the composition to self-heating is concerned, the level of neutral sodium phosphates combined with sodium sulphate and chloride may be as high as 30 percent by weight. In actuality, however, already at a phosphate level in excess of 15 percent by weight, the composition turns alkaline and loses much of its bactericidal effectiveness. The minimal level of sodium chloride and sulphate equal to 40 percent by weight is determined by the need that the overall quantity of inorganic components account for at least 55 percent by weight of the total, for otherwise the composition loses its stability to self-heating. The inorganic constituent may be raised to 60 percent by weight and even higher, but this is hardly useful as the level of DCDMH in the composition will be decreased accordingly. The quantity of the wetting agent (alkyl- or alkylarylsulphonate) is limited to 1-5 percent by weight by the fact that below this range the composition is poorly wetted and solubilizes slowly, while above the range the composition loses its stability to self-heating and the process solutions experience extensive frothing, hampering the use of the preparation for mechanical washing and disinfection.

Further research demonstrated that the proposed bactericide could safely include certain dopants improving the appearance and consumer properties of the preparation: components reducing the smell of chlorine such as sodium metasilicate incorporated in the composition at the rate of up to 5 percent by weight; dyes resistant to chlorine compounds such as ultramarine or azurine incorporated in the composition at the rate of up to 1 percent by weight; or odoriferous substances. To reduce the dusting of the preparation in the course of manufacture, packing and application, it is possible to employ up to 2 percent by weight of saturated petroleum products melting at temperatures above 350° C., e.g. chlorinated biphenyls. In this case the process solutions acquire opalescence which, however, fails to affect their applicability, e.g. for the purpose of general disinfection. In general, such dopants can always be added to the proposed composition and the question as to their use depends entirely on the ultimate application of the preparation.

The bactericide of this invention may include a range of components listed in Table 6.

The proposed bactericide offers important advantages of stability to self-heating, which makes for safety in the manufacture and storage thereof, and a high level of active chlorine.

At the same time, the proposed preparation is readily soluble in water, making it possible to reach a high concentration of active chlorine in water. The rate of its dissolution in water is likewise quite high: 0.2 percent by weight of the preparation solubilizes within 10 seconds to the extent of 96 to 98 percent of active chlorine, forming no film on the surface of the solution. The proposed bactericide has a potent effect on microorganisms: at a concentration of 0.005 percent by weight it kills E.coli and Staphyllococcus aureus within 5 to 15 minutes. The process solutions of the proposed preparation have a pH of from 6 to 7, i.e. close to the pH value of tap water, so that the bactericide has no irritating effect on the operators' skin. The median lethal dose $LD_{50}$ of the proposed bactericide amounts to 2,000–3,000 mg/kg of weight for warm-blooded animals, i.e. its toxicity is quite low. At a concentration of 0.2 percent by weight and higher, the proposed bactericide exhibits excellent detergency.

Table 6

| Components level, wt.% | | | | | | | | | | | | |
| --- | --- | --- | --- | --- | --- | --- | --- | --- | --- | --- | --- | --- |
| 1,3-dichloro-5,5-dimethyl-hydantoin | 22.1 | 22.1 | 22.1 | 22.1 | 22.1 | 22.1 | 19.1 | 19.1 | 22.1 | 22.1 | 22.1 | 19.1 |
| 5,5-dimethyl-hydantoin | 14.4 | 14.4 | 14.4 | 14.4 | 14.4 | 14.4 | 14.4 | 12.4 | 14.4 | 14.4 | 14.4 | 12.4 |
| sodium tri-phosphate | — | 3.0 | 10.0 | — | 5.0 | 10.0 | 5.0 | 5.0 | — | — | 5.0 | 5.0 |

Table 6-continued

| Components level, wt.% | | | | | | | | | | | | |
|---|---|---|---|---|---|---|---|---|---|---|---|---|
| sodium tripolyphosphate | 10.0 | 7.0 | — | 10.0 | 5.0 | — | 10.0 | 10.0 | 10.0 | 10.0 | 5.0 | 5.0 |
| sodium chloride | 50.0 | 50.0 | 50.0 | 50.0 | 50.0 | 50.0 | — | — | 30.0 | 45.0 | 50.0 | — |
| anhydrous sodium sulphate | 3.5 | 3.5 | 3.5 | 3.5 | 3.5 | 3.5 | 50.0 | 50.0 | 0.0 | 5.0 | — | 50.0 |
| alkylaryl-sulphonate | 3.5 | 3.5 | 3.5 | — | — | — | 3.5 | — | .5 | — | 2.0 | 1.5 |
| alkylsulphonate | — | — | — | 3.5 | 3.5 | 3.5 | — | 3.5 | — | 3.5 | 1.5 | 2.0 |

If stored properly, the bactericide of the invention remains active for 3 to 4 years. The proposed bactericide is easy to manufacture, for its air-dust mixtures present no explosion hazard.

The invention will be further understood from the following exemplary embodiments thereof.

EXAMPLE 1

A bactericide of the following composition, wt.%:
1,3-dichloro-5,5-dimethylhydantoin, 22.1
5,5-dimethylhydantoin, 14.4
sodium tripolyphosphate, 10.0
sodium chloride, 50.0
hexadecylsulphonate, 3.5.

Tested for stability to self-heating according to the technique described hereabove (at a heating gradient of 2° C. per minute), the bactericide showed no temperature jump. A 0.005-weight percent solution of the bactericide killed vegetative bacteria within 5 to 15 minutes; a 0.05 -percent solution thereof killed viruses within 50 minutes.

The toxicity of the bactericide was low: its $LD_{50}$ was 2,850 mg/kg of weight for rats and 2,500 mg/kg of weight for mice.

The composition was completely dissolved in water at the rate of 25 g/lit. At 2 g/lit, the bactericide was dissolved in water within 10 seconds to the extent of 97 percent (in terms of active chlorine), forming no film on the surface of the solution or on the walls of the vessel.

At a concentration of from 0.2 to 0.5 percent by weight, the bactericide proved an effective detergent and can thus be employed for washing and disinfecting various surfaces.

EXAMPLE 2

A bactericide of the following composition, wt.%:
1,3-dichloro-5,5-dimethylhydantoin, 22.1
5,5-dimethylhydantoin, 14.4
sodium tripolyphosphate, 10.0
sodium chloride, 30.0
anhydrous sodium sulphate, 20.0
hexadecylsulphonate, 3.5.

Tested for stability to self-heating under conditions as specified in Example 1, the bactericide showed no temperature jump.

Vegetative bacterial forms were killed by a 0.005-weight percent solution of the bactericide within 5 to 15 minutes. The composition was completely dissolved in water at the rate of 25 g/lit. The process solutions of the bactericide formed no film on the surface of the solution or on the vessel walls.

EXAMPLE 3

A bactericide of the following composition, wt.%:
1,3-dichloro-5,5-dimethylhydantoin, 19.1
5,5-dimethylhydantoin, 12.4
sodium tripolyphosphate, 7.0
sodium chloride, 50.0
heptadecylsulphonate, 3.5.

Tested for stability to self-heating under conditions as specified in Example 1, the bactericide showed no temperature jump. The bactericide was completely dissolved in water at the rate of 30 g/lit. At 2 g/lit, the bactericide was dissolved in water to the extent of 98 percent by weight in terms of active chlorine within 10 seconds and completely within 15 seconds. At a concentration of from 0.2 to 0.5 percent by weight, the bactericide exhibited good detergency and can thus be employed for washing and disinfecting various surfaces in a single-step procedure.

EXAMPLE 4

A bactericide of the following composition, wt.%:
1,3-dichloro-5,5-dimethylhydantoin, 25.0
5,5-dimethylhydantoin, 19.0
sodium tripolyphosphate, 15.0
sodium chloride, 40.0
sodium dodecylbenzenesulphonate, 1.0.

Tested for stability to self-heating under conditions as specified in Example 1, the bactericide showed no temperature jump.

The bactericide was completely dissolved in water at the rate of 25 g/lit.

EXAMPLE 5

A bactericide of the following composition, wt.%:
1,3-dichloro-5,5-dimethylhydantoin, 22.0
5,5-dimethylhydantoin, 14.5
sodium tripolyphosphate, 5.5
sodium triphosphate, 5.5
sodium chloride, 49.5
sodium dodecylbenzenesulphonate, 3.0.

Tested for stability to self-heating under conditions as specified in Example 1, the bactericide showed no temperature jump.

The bactericide was completely dissolved in water at the rate of 27 g/lit.

EXAMPLE 6

A bactericide of the following composition, wt.%:
1,3-dichloro-5,5-dimethylhydantoin, 22.1
5,5-dimethylhydantoin, 14.5
sodium triphosphate, 11.0
anhydrous sodium sulphate, 49.4
sodium dodecylbenzenesulphonate, 3.0.

Tested for stability to self-heating under conditions as specified in Example 1, the bactericide showed no temperature jump.

The bactericide was completely dissolved in water at the rate of 26 g/lit; at process concentrations, it formed no film on the surface of the solution or on the walls of the vessel.

EXAMPLE 7

A bactericide of the following composition, wt.%:
1,3-dichloro-5,5-dimethylhydantoin, 22.0

5,5-dimethylhydantoin, 14.5
sodium tripolyphosphate, 11.0
anhydrous sodium sulphate, 49.5
sodium dodecylbenzenesulphonate, sulphonate, 3.0.

Tested for stability to self-heating under conditions as specified in Example 1, the bactericide showed no temperature jump.

The bactericide was completely dissolved in water at the rate of 26 g/lit; at process concentrations, it formed no film on the surface of the solution or on the walls of the vessel.

EXAMPLE 8

A bactericide of the following composition, wt.%:
1,3-dichloro-5,5-dimethylhydantoin, 22.0
5,5-dimethylhydantoin, 14.5
sodium triphosphate, 11.0
sodium chloride, 49.5
sodium dodecylbenzenesulphonate, 3.0.

Tested for stability to self-heating under conditions as specified in Example 1, the bactericide showed no temperature jump.

The bactericide was completely dissolved in water at the rate of 27 g/lit and formed no film at the process concentration.

EXAMPLE 9

A bactericide of the following composition, wt.%:
1,3-dichloro-5,5-dimethylhydantoin, 19.0
5,5-dimethylhydantoin, 14.0
sodium tripolyphosphate, 7.0
sodium chloride, 40.0
anhydrous sodium sulphate, 5.0
sodium dodecylbenzenesulphonate, 5.0.

Tested for stability to self-heating under conditions as specified in Example 1, the bactericide showed no temperature jump.

The bactericide was completely dissolved in water at the rate of 28 g/lit; at process concentrations, it formed no film on the surface of the solution or on the walls of the vessel. At a concentration of from 0.2 to 0.5 percent by weight, it exhibited adequate detergency and can thus be employed for washing and disinfecting various surfaces in a single-step procedure.

EXAMPLE 10

A bactericide of the following composition, wt.%:
1,3-dichloro-5,5-dimethylhydantoin, 19.0
5,5-dimethylhydantoin, 10.0
sodium tripolyphosphate, 7.0
sodium chloride, 55.0
anhydrous sodium sulphate, 7.0
hexadecylsulphonate, 2.0

Tested for stability to self-heating under conditions as specified in Example 1, the bactericide showed no temperature jump.

The bactericide was completely dissolved in water at the rate of 28 g/lit; at the process concentrations, it formed no film on the surface of the solution or on the walls of the vessel.

EXAMPLE 11

A bactericide of the following composition, wt.%:
1,3-dichloro-5,5-dimethylhydantoin, 25.0
5,5-dimethylhydantoin, 19.0
sodium tripolyphosphate, 15.0
sodium chloride, 40.0
sodium dodecylbenzenesulphonate, 1.0
anhydrous sodium metasilicate, 4.0
saturated petroleum fraction having a melting point above 350° C., 1.0.

Tested for stability to self-heating under conditions as specified in Example 1, the bactericide showed no temperature jump.

The bactericide was dissolved in water at the rate of 3 g/lit in less than 10 seconds to the extent of 95 percent by weight in terms of active chlorine and formed a strongly opalescing fluid which remained stable for 24 hours.

What is claimed is:

1. A readily water soluble bactericide which is stable to self-heating upon manufacture and storage, said bactercide consisting essentially of 1, 3-dichloro-5,5-dimethylhydantoin in an amount of 19 to 25% by weight; 5,5-dimethylhydantoin in an amount of 10 to 19% by weight; a neutral sodium phosphate in an amount of 7 to 15% by weight; a sodium salt selected from the group consisting of sodium chloride, anhydrous sodium sulphate and a mixture thereof in an amount of 59 to 40% by weight; and a surface-active agent selected from the group consisting of an alkylarylsulphonate, an alkylsulphonate and a mixture thereof in an amount of 5 to 1% by weight.

2. The bactericide of claim 1, which has the following composition, wt.%:
1,3-dichloro-5,5-dimethylhydantoin, 22.1
5,5-dimethylhydantoin, 14.4
a neutral sodium phosphate, 10.0
sodium chloride, 50.0
alkylarylsulphonate, 3.5.

3. The bactericide of claim 1, which has the following composition, wt.%:
1,3-dichloro-5,5-dimethylhydantoin, 22.1
5,5-dimethylhydantoin, 14.4
a neutral sodium phosphate, 10.0
sodium chloride, 50.0
alkylsulphonate, 3.5

4. The bactericide of claim 1, which has the following composition, wt.%:
1,3-dichloro-5,5-dimethylhydantoin, 19.1
5,5-dimethylhydantoin, 12.4
a neutral sodium phosphate, 15.0
anhydrous sodium sulphate, 50.0
alkylarylsulphonate, 3.5

5. The bactericide of claim 1, which has the following composition, wt.%:
1,3-dichloro-5,5-dimethylhydantoin, 19.1
5,5-dimethylhydantoin, 12.4
a neutral sodium phosphate, 15.0
anhydrous sodium sulphate, 50.0
alkylsulphonate, 3.5

6. The bactericide of claim 1, which has the following composition, wt.%:
1,3-dichloro-5,5-dimethylhydantoin, 22.1
5,5-dimethylhydantoin, 14.4
a neutral sodium phosphate, 10.0
sodium chloride and anhydrous sodium sulphate, 50.0
alkylsulphonate, 3.5.

7. The bactericide of claim 1, which has the following composition, wt.%:
1,3-dichloro-5,5-dimethylhydantoin, 22.1
5,5-dimethylhydantoin, 14.4
a neutral sodium phosphate, 10.0
sodium chloride and anhydrous sodium sulphate, 50.0
alkylarylsulphonate, 3.5.

8. The bactericide of claim 1, which has the following composition, wt.%:
1,3-dichloro-5,5-dimethylhydantoin, 22.1
5,5-dimethylhydantoin, 14.4
a neutral sodium phosphate, 10.0
sodium chloride, 50.0
alkyarylsulphonate and alkylarylsulphonate 3.5.

9. The bactericide of claim 1, which has the following composition, wt.%:
1,3-dichloro-5,5-dimethylhydantoin, 19.1
5,5-dimethylhydantoin, 12.4
a neutral sodium phosphate, 15.0
anhydrous sodium sulphate, 50.0
alkylarylsulphonate and alkylsulphonate 3.5.

* * * * *